(12) United States Patent
Rawlings et al.

(10) Patent No.: US 8,835,496 B2
(45) Date of Patent: Sep. 16, 2014

(54) DERMATOLOGICAL COMPOSITIONS COMPRISING A FAT OR OIL OF AN ESSENTIAL FATTY ACID TRIGLYCERIDE FOR TREATING OF SKIN, MUCOSA, HAIR, NAILS, OR SCALP

(75) Inventors: Anthony Vincent Rawlings, Northwich (GB); Debra Louise Jones, Selby (GB)

(73) Assignee: Croda International PLC, Goole, North Humberside (GB)

( * ) Notice: Subject to any disclaimer, the term of this patent is extended or adjusted under 35 U.S.C. 154(b) by 22 days.

(21) Appl. No.: 13/512,278

(22) PCT Filed: Nov. 9, 2010

(86) PCT No.: PCT/GB2010/002043
§ 371 (c)(1),
(2), (4) Date: May 25, 2012

(87) PCT Pub. No.: WO2011/064524
PCT Pub. Date: Jun. 3, 2011

(65) Prior Publication Data
US 2012/0289596 A1    Nov. 15, 2012

(30) Foreign Application Priority Data

Nov. 27, 2009   (GB) .................................. 0920846.3

(51) Int. Cl.
*A61K 31/22*    (2006.01)
*A61K 31/20*    (2006.01)
*A61K 31/232*   (2006.01)
*A61K 31/231*   (2006.01)
*A61K 31/202*   (2006.01)
*A61K 31/201*   (2006.01)
*A61K 31/00*    (2006.01)

(52) U.S. Cl.
CPC ............. *A61K 31/201* (2013.01); *A61K 31/232* (2013.01); *A61K 31/231* (2013.01); *A61K 31/202* (2013.01); *A61K 31/00* (2013.01)
USPC ............ 514/547; 514/558; 514/559; 514/560

(58) Field of Classification Search
USPC .................................. 514/547, 558, 559, 560
See application file for complete search history.

(56) References Cited

FOREIGN PATENT DOCUMENTS

| | | |
|---|---|---|
| EP | 0582834 | 2/1994 |
| EP | 1163905 | 12/2001 |
| EP | 1671629 | 6/2006 |
| GB | 2453157 | 4/2009 |
| JP | 9-143067 | 6/1997 |
| JP | 2000-95683 | 4/2000 |
| WO | WO 97/46219 | 12/1997 |
| WO | WO 97/46220 | 12/1997 |
| WO | WO 2006/004582 | 1/2006 |

OTHER PUBLICATIONS

International Search Report dated Jan. 12, 2011 for PCT/GB2010/002043.

*Primary Examiner* — Kevin E Weddington
(74) *Attorney, Agent, or Firm* — Jones Day

(57) ABSTRACT

The present invention relates to a human beta-defensin inducing agent that comprises at least one fat or oil of an essential fatty acid triglyceride or a derivative thereof as the main active ingredient. It also relates to cosmetic, dermatological and pharmacological formulations comprising the at least one fat or oil.

10 Claims, 1 Drawing Sheet

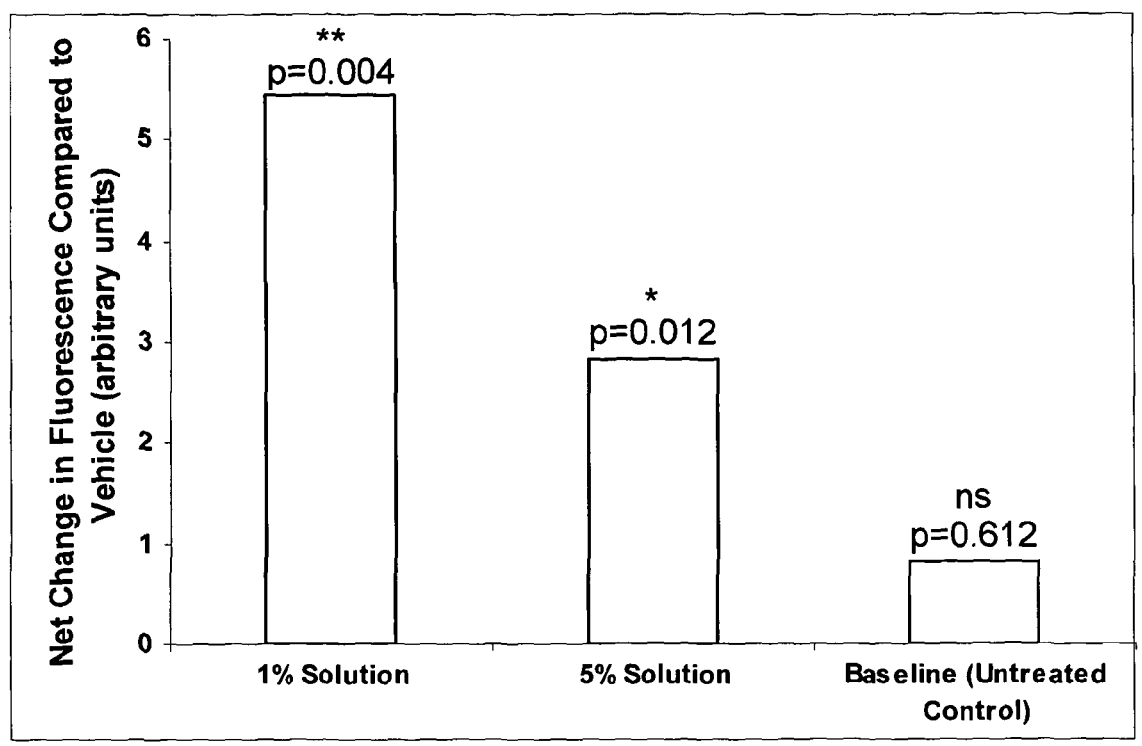

DERMATOLOGICAL COMPOSITIONS COMPRISING A FAT OR OIL OF AN ESSENTIAL FATTY ACID TRIGLYCERIDE FOR TREATING OF SKIN, MUCOSA, HAIR, NAILS, OR SCALP

CROSS REFERENCE TO RELATED APPLICATION

This application is the National Phase application of International Application No. PCT/GB2010/002043, filed Nov. 9, 2010, which designates the United States and was published in English. This application, in its entirety, is incorporated herein by reference.

The present invention relates to a human beta-defensin inducing agent that comprises at least one fat or oil of an essential fatty acid triglyceride or a derivative thereof as the main active ingredient. The present invention relates to cosmetic, dermatological and pharmacological formulations comprising the at least one fat or oil.

The human skin is in permanent contact with various pathogenic micro-organisms but still typically remains free from signs of infection. This is due to the physical barrier of the skin and also to the synthesis of several antimicrobial agents. These antimicrobial agents form a part of the innate immune system of the skin which is the first line of defense against microbial infection. Many peptides have been discovered that have antimicrobial activity. Antimicrobial peptides are small, cationic, amphiphilic peptides of 12 to 50 amino acids which have microbial activity against bacteria, fungi, protozoa and viruses. Mammalian defensins are one sub set of antimicrobial peptides which are subdivided into three main classes, namely alpha-defensins, beta-defensins and theta-defensins. Mammalian alpha-defensins are predominately found in neutrophils and in small intestinal Paneth cells whereas mammalian beta-defensins have been isolated from both leukocytes and epithelial cells. Beta-defensins are known to be expressed in the mucosa and in the epithelia cells of the skin, lungs, trachea, tongue, tonsils, saliva, kidneys and genitals. Six types of Beta-defensin have been currently isolated and their structures identified i.e. human beta-defensin-1 (hBD-1) to hBD-6 respectively, hBD-2 and hBD-3 can both be induced in the human body, hBD-2 in the skin, trachea and lungs and hBD-3 in the skin, trachea, tonsils and tongue. hBD-2 is synthesised and stored in lamellar bodies of keratinocytes within the spinous and granular layer of the skin and hBD-2 levels in the skin are normally very low. The hBD-2 is released during differentiation and after skin barrier disruption, for example in times of inflammation to protect the skin, wounds and burns. Examples of times of inflammation to protect the skin include during prolonged sun exposure, bacterial infection, skin diseases such as psoriasis and acne vulgaris lesions. hBD-2 has been shown to have excellent antimicrobial activity against certain bacteria, namely *Escherichia coli, Pseudomonas aeruginosa*, which is a common cause of burn infections, and along with hBD-3 against *Staphylococcus aureus*, which is the most common single isolate in wounds in mammals with diabetes. hBD-2 has also been shown to have excellent antimicrobial activity against certain fungi, for example *Candida albicans*.

The expression of human beta-defensins is known to be enhanced at cutaneous wound sites. Burn wounds are associated with high levels of circulating pro-inflammatory cytokines and immunosuppression, promoting systemic inflammatory response syndrome and sepsis. Beta-defensins, in particular hBD-2, have been identified at burn sites and are believed to participate in burn wound healing.

As well as the above properties associated with the innate immune system hBD-2 has also been found to have chemotactic properties for immature dendritic cells, some types of T and B-lymphocytes, neutrophils and macrophages, and act as adjuvants which can enhance adaptive immunity.

The presence of beta-defensins in the skin is one of the factors that can protect the skin and keep it healthy. Therefore the increase of beta-defensins is a potential benefit to human skin and as such is to be encouraged. Two possible mechanisms of increasing the beta-defensins are to

- synthesise molecules that have structures similar to those of the known isolated beta-defensins and/or
- provide a mechanism for the induction of the naturally occurring beta-defensins.

One mechanism for the induction of the beta-defensins is to provide ingredients to the human body, topically and/or orally that can promote induction of the beta-defensins.

Fats and oils are triesters of glycerol and are typically known as triglycerides. If the triglyceride is solid at room temperature then it is generally considered to be a fat. If it is liquid at room temperature then it is generally considered to be an oil, Most triglycerides in animals are fats whilst most triglycerides in vegetables, fruit, marine, plants and their seeds tend to be oils. Fatty acids can be obtained from fats or oils by hydrolysis. Essential fatty acids in humans are fatty acids that cannot be constructed within an organism from other components by any known chemical pathways and therefore must be obtained from the human diet. There are two families of essential fatty acids, omega-3 and omega-6. Essential fatty acids are a subset of polyunsaturated fatty acids. Polyunsaturated fatty acids are aliphatic monocarboxylic acids having at least two double bonds, either cis or trans, conjugated or non-conjugated. For essential fatty acids the double bonds are all cis and separated by a methylene group.

EP1671629 A1 discloses a human beta-defensin secretion promoter that can be used in various forms such as internal preparations, external preparations and foods where the promoter is an organic acid which is preferably at least one member selected from the group consisting of fumaric acid, malic acid, citric acid, ascorbic acid, lactic acid, acetic acid, adipic acid, tartaric acid, cinnamic acid, glutamic acid and succinic acid. In this invention because human beta-defensin secretion promotion effects observed in the labial region and inside the oral cavity are excellent this is where the organic acids are applied. Other organic acids are disclosed in EP1671629 A1 but there is no disclosure of any polyunsaturated fatty acids.

GB2391476 A discloses a range of active ingredients which induce the expression of hBD-2 and/or hBD-3 without triggering inflammatory, irritation or intolerance reactions. The range of active ingredients is i) an extract of any of the group consisting of artemisia root, Canadian erigeron, elderberry bark, rupturewort, pineapple juice, peppermint, areca, cocoa, quinoa, arnica, boldo, sarsaparilla, walnut leaf, hibiscus flower, pumpkin, sunflower, peony, St John's Wort and horse chestnut or ii) jasmonic acid or vitamin A, derivatives or precursors of or iii) isoleucine ester. There is no disclosure of any triglycerides of essential fatty acids or triglyceride derivatives as beta-defensin promoters.

The present invention is based on our discovery that a fat or oil containing at least one of an essential fatty acid triglyceride or corresponding triglyceride derivative has been found to induce beta-defensin secretions in the human body, in particular in human skin.

Accordingly the present invention provides a human beta-defensin inducing agent comprising at least one fat or oil of an essential fatty acid triglyceride or a derivative thereof as the main active ingredient.

Human beta-defensin encompasses human beta-defensin 1, human beta-defensin 2, human beta-defensin 3, human beta-defensin 4, human beta-defensin 5 and human beta-defensin 6. Preferably it encompasses human beta-defensin 1, human beta-defensin 2 and human beta-defensin 3, more preferably human beta-defensin 2 and human beta-defensin 3 and especially human beta-defensin 2.

The human beta-defensin inducing agent comprises at least one fat or oil of an essential fatty acid triglyceride or derivative thereof. By derivative thereof we include essential fatty acids themselves and ethyl esters thereof. The oil or fat of the essential fatty acid triglyceride can be processed to convert it, at least partially, to the corresponding essential fatty acid. The processing typically involves a saponification step to hydrolyse the triglyceride followed by an acidification step and then at least one separation step to remove the corresponding essential fatty acid.

Suitable essential fatty acid triglyceride or derivatives thereof include triglycerides of both main series of essential fatty acids i.e. omega-6 and omega-3 and their corresponding fatty acids and fatty acid ethyl esters. Examples include triglycerides of cis 7, 10, 13-hexadecatrienoic acid, linoleic acid, $\alpha$-linoleic acid, $\gamma$-linoleic acid, stearidonic acid, eicosadienoic acid, dihomo-$\gamma$-linoleic acid, eicosatrienoic acid, eicosatetraenoic acid, arachidonic acid, eicosapentaenoic acid, docosadienoic acid, adrenic acid, docosapentaenoic acid, docosahexaenoic acid and tetracosapentaenoic acid and their corresponding acids. Especially preferred triglycerides include those of linoleic acid, $\alpha$-linoleic acid, $\gamma$-linoleic acid and stearidonic acid.

Preferably the human beta-defensin inducing agent comprises a mixture of fats or oils of an essential fatty acid triglycerides or derivatives thereof. Especially preferred is a mixture of oils of essential fatty acid triglycerides or derivatives thereof of linoleic acid, $\alpha$-linoleic acid, $\gamma$-linoleic acid and stearidonic acid. Within this especially preferred mixture preferable ranges of each ingredient are 5 to 25% by weight linoleic acid, 20 to 55% by weight $\alpha$-linoleic acid, 2 to 15% by weight $\gamma$-linoleic acid and 8 to 25% by weight stearidonic acid.

The human beta-defensin inducing agent preferably comprises at least one oil of an essential fatty acid triglyceride or derivative thereof. Preferably the at least one oil of an essential fatty acid triglyceride is derived from a natural source. Preferably the at least one oil of an essential fatty acid triglyceride is extracted from a vegetable, plant, marine material or fruit or extracted from seeds of vegetables, plants or fruit.

One preferred source for the at least one oil of an essential fatty acid triglyceride is the seeds of the family of Boraginaceae, which is a large plant family with approximately 100 genera and 2500 species which are widely distributed throughout the northern hemisphere. Even more preferred are the seeds of the genus Echium which itself contains about 30 species distributed across Europe, the Mediterranean region, Madeira, the Canaries and the Azores. Especially preferred are the seeds of *Echium plantagineum* and *Echium vulgaris*. Oil extracted from the seeds of *Echium plantagineum* and *Echium vulgaris* have been found to contain the fatty acid triglcerides of linoleic acid, $\alpha$-linoleic acid, $\gamma$-linoleic acid and stearidonic acid. Table 1 below indicates typical levels of these fatty acid triglycerides in oil extracted from the seeds of *Echium plantagineum* and *Echium vulgaris* along with other fatty acids, which are not essential fatty acids that are present in the oil extract. Note that these levels may vary depending on the crop of seeds from which the oil is extracted.

TABLE 1

| Fatty Acid (Triglyceride of) | Echium Vulgaris (wt %) | Echium Planagineum (wt %) |
|---|---|---|
| Palmitic acid | 6.2 | 7.6 |
| Stearic acid | 2.0 | 3.8 |
| Oleic acid | 8.0 | 16.7 |
| Linoleic acid | 10.3 | 16.0 |
| $\gamma$-linoleic acid | 5.3 | 11.9 |
| $\alpha$-linoleic acid | 47.3 | 29.9 |
| Stearidonic acid. | 19.8 | 12.3 |
| Other | 1.1 | 1.8 |

Another preferred source for the at least one oil of an essential fatty acid triglyceride is the seeds of the family of Linum, which is a genus of approximately 200 species in the flowering plant Linaceae. Even more preferred are the seeds of the genus *Linum usitatissimum*. Oil extracted from these seeds which is known as linseed oil or flax seed oil has been found to contain the fatty acid trigylcerides of linoleic acid and $\alpha$-linoleic acid.

Table 2 below indicates typical levels of these fatty acid triglycerides in oil extracted from these seeds of along with other fatty acids, which are not essential fatty acids that are present in the oil extract. Note that these levels may vary depending on the crop of seeds from which the oil is extracted.

TABLE 2

| Fatty Acid (Triglyceride of) | *Linum usitatissimum* (wt %) |
|---|---|
| Palmitic acid | About 7.0 |
| Stearic acid | 3.4 to 4.6 |
| Oleic acid | 18.5 to 22.6 |
| Linoleic acid | 14.2 to 17.0 |
| $\alpha$-linoleic acid | 51.9 to 55.2 |
| Other | 0.0 to 5.0 |

The at least one fat or oil of an essential fatty acid triglyceride or a derivative thereof is present in the human beta-defensin inducing agent preferably at a concentration of between 0.01 to 20% by weight and more preferably 0.1 to 10% by weight. More preferably, the at least one fat or oil of an essential fatty acid triglyceride or a derivative thereof is present in the human beta-defensin inducing agent at a concentration of between 0.5 to 7% by weight, desirably between 1 and 5% by weight.

The human beta-defensin inducing agent can be applied topically to the skin and also to wounds of the skin of all parts of the human body to induce human beta-defensin secretion by adding it to a pharmacological, dermatological or cosmetic formulation. It can also be applied topically to any/all of mucosa, hair, nails and scalp.

Preferably, the human beta-defensin inducing agent is applied topically to the skin or oral mucosa.

A further preferred aspect of the invention provides a dermatological formulation comprising 0.01 to 20% by weight of a human beta-defensin inducing agent comprising at least one fat or oil of an essential fatty acid triglyceride or a derivative thereof as the main active ingredient.

A further aspect of the invention provides a pharmacological formulation comprising 0.01 to 20% by weight of a human beta-defensin inducing agent comprising at least one fat or oil of an essential fatty acid triglyceride or a derivative thereof as the main active ingredient.

A further aspect of the invention provides a cosmetic formulation comprising 0.01 to 20% by weight of a human beta-defensin inducing agent comprising at least one fat or oil of an essential fatty acid triglyceride or a derivative thereof as the main active ingredient.

Pharmacological formulation includes medicine, quasi-drug and medical product. Medical product includes adhesive plaster, bandage, dressing. Cosmetic formulation includes cream, emulsion, lotion, gel and oil for the skin (for example hands, face, feet), soap, for example toilet soap and deodorant soap, bath and shower preparation in the form of salt, foam, oil, gel, depilatories, deodorant and anti-perspirant, shaving product in the form of creams, foams and lotions, products intended for application to the lips, products intended for care of the teeth and the mouth, products for nail care and make up, products for external intimate hygiene, sun bathing products, skin whitening products and anti-wrinkle products. Dermatological topical formulation includes cream, lotion, milk, oil, ointment and gel. The form of the pharmacological, dermatological or cosmetic formulation is not limited as long as it can be applied to the skin, mucosa, hair, nails, scalp or wounds of the skin. Suitable forms include liquid, milky lotion, powder, suspension, cream, ointment, mousse, gel, jelly, paste, solid stick, aerosol, spray, liniment, serum, impregnated into bandage, dressing, patch or adhesive plaster and needle free jet injection.

The human beta-defensin secretion inducing agent may consist of the above active ingredient or it may comprise base materials and/or carriers and additives that are cosmetically, dermatologically and pharmacologically acceptable along with the active ingredient. Also it may comprise further active ingredients. Such further active ingredients may be contained within carriers.

Examples of suitable base materials include water, surfactants, oils and waxes, fatty alcohols, emulsifiers, silicones, humectants, thickening or gelling agents.

Examples of suitable carriers include lipophilic oils including emollient esters, emollient ethers, fatty acids, other triglycerides, mineral oils and other petrochemical derivatives, silicones, solvents, surfactants based solubilisation systems, penetration enhancement molecules, liposome and other encapsulation systems.

Examples of suitable additives include gelling agents, preservatives, oils, solvents, antioxidants, scents, charges, pigments, filters, odour absorbers, surfactants, dispersants, pH adjustors, thickeners and dyes. Preferable additives include antioxidants. Examples of additive types which are specifically known to be effective in pharmacological formulations include humectant, vitamins, plant extract, astringent, whitening agent, cell activator, vasodilator, circulation accelerator, skin hyperergasia agent, antiallergic agent, antihistamine.

Dependant on the specific formulation some materials may be defined as base, carrier, additive and/or active.

Examples of further active ingredients include other anti-bacterial actives, moisturiser, surfactant, UV blocking/absorbing, anti acne, antioxidant, anti-inflammatory, wound healing and anti ageing agents.

Examples of suitable applications areas for the pharmacological formulation include treatment of wounds. Types of wounds include burns (first, second and third degree) caused by sun exposure or scalding and wounds caused by cuts. Other examples include use in sanitising gels and lotions for application to the skin.

Examples of suitable application areas for the dermatological formulation include treatment of skin disorders, for example eczema, dermatitis and furuncles, in particular treatment of both adult and child dermatitis. Specifically preferred is treatment of atopic dermatitis and diaper dermatitis for babies and toddlers.

A further aspect of the invention provides use of a human beta-defensin inducing agent comprising at least one fat or oil of an essential fatty acid triglyceride or a derivative thereof as the main active ingredient for the manufacture of a pharmacological formulation to exert an antimicrobial effect on treated skin or skin wounds.

A further aspect of the invention provides use of a human beta-defensin inducing agent comprising at least one fat or oil of an essential fatty acid triglyceride or a derivative thereof as the main active ingredient for the manufacture of a cosmetic formulation to exert an antimicrobial effect on treated skin, mucosa, hair, nails and scalp. A further aspect of the invention provides use of a human beta-defensin inducing agent comprising at least one fat or oil of an essential fatty acid triglyceride or a derivative thereof as the main active ingredient for the manufacture of a dermatological formulation to exert an antimicrobial effect on treated skin.

The human beta-defensin inducing agent can also be applied orally, for example by adding it to a internal use medicine, an internal use quasi-drug, a foodstuff, a dietary supplement (for example a vitamin containing supplement), toothpaste and mouthwash.

A further aspect of the invention provides use of at least one fat or oil of an essential fatty acid triglyceride or a derivative thereof to induce human beta-defensin secretion in the human body.

Any of the above features of the invention may be taken either independently or in combination with any one or more other features of the invention in any combination, and with any aspect of the invention.

The following examples and the accompanying drawing illustrate the invention. All parts and percentages are by weight unless otherwise stated.

In the drawing FIG. 1 is a graphical representation of the results obtained in Example 2 using a 1-sample t-test statistical analysis

EXAMPLE 1

10 kg of the seeds of *Echium plantagineum* were crushed and the oil extracted with 15 liters of petroleum ether. The extract was evaporated to yield 1741 g of an oil which was converted to the corresponding fatty acid methyl esters and analysed by gas chromatography. The fatty acid profile of the converted oil was as shown in Table 3 below

TABLE 3

| Essential fatty acid (methyl esters of) | Essential Fatty acid content (wt %) |
|---|---|
| Palmitic | 7.2 |
| Stearic | 4.0 |
| Oleic | 18.2 |
| Linoleic | 16.5 |
| γ-linoleic acid | 11.8 |
| α-linoleic acid | 28.9 |
| Stearidonic acid. | 12.2 |
| Other | 1.2 |

EXAMPLE 2

(This work was carried out in conjunction with Dermatological Sciences Research group, School of Transitional Medicine, The University of Manchester)

Solutions containing 30 μl of 1% solution (% by wt) of the oil extracted in Example 1 in Crodamol™ IPM vehicle (carrier), 30 μl of 5% solution of the oil extracted in Example 1 in Crodamol™ IPM (available ex Croda Europe Ltd) and 30 μl of Crodamol™ IPM were applied separately to each of fourteen healthy but clinically aged volunteers (age range 41-78) under standard 6 mm diameter Finn chambers to the extensor aspect of the forearm. For each volunteer an untreated area was also occluded to provide a baseline control. The formulations were applied to clean skin on days 1, 4 and 8 of the assay. On day 12 the Finn chambers were removed and 3 mm punch biopsies were obtained under 1% lignocaine anaesthesia from each of the test sites on the forearm. The biopsies were embedded in OCT compound (Tissue-Tek®) and snap frozen in liquid nitrogen. The frozen biopsies were sectioned and placed onto glass slides. The slides were fixed in ice-cold acetone at −20° C. for 10 minutes and then blocked in 10% normal donkey serum for 90 minutes. Following blocking, the sections were washed briefly in phosphate buffered saline (PBS) and a primary antibody raised against hBD-2 was applied at a dilution of 1:200 overnight at 4° C. The following morning, the slides were washed in PBS twice and then with PBS t 0.05% Tween™-20 (available ex Croda Europe Ltd) for 5 minutes. A secondary antibody raised against hBD-2 was then added at a dilution of 1:100 for 60 minutes at room temperature. The sections were then extensively washed in PBS and mounted using a 4'-6-Diamidino-2-phenylindole (DAPI) stain. The sections were viewed using a fluorescent microscope and pictures taken at a magnification ×13 under the same exposure settings for all slides.

Each volunteer had 4 test sites. 3 sections from each test site were stained per volunteer. The background and epidermal staining were quantified using ImageJ software (available ex National Institute of Health (NIH)) and subtracted. The net difference was calculated compared to the average value of the vehicle and a 1 sample t-test carried out to determine significance. The study and analysis was carried out blind.

FIG. 1 illustrates the results.

The p values for 1% and 5% of the 1-sample t-test show that the results are indeed significant.

FIG. 1 demonstrates that presence of both 1% and 5% of the human beta-defensin inducing agent according to the invention promotes the formation of human beta-defensin 2 when applied topically to human skin.

It was found that no positive benefit was observed when the vehicle was applied topically to the skin when compared to the untreated control.

When net differences were calculated from the treatment to the vehicle, no significance was met with the untreated site demonstrating the control did not have a positive effect on hBD-2 expression.

EXAMPLE 3

A cosmetic emulsion was prepared from the following ingredients in Table Four.

TABLE 4

| Ingredient | Chemical composition | % w/w |
|---|---|---|
| Oil Phase: | | |
| Crill 3 [1] | Sorbitan Stearate | 1.20 |
| Crillet 3 [1] | Polysorbate 60 | 1.80 |
| Crodamol IPM [1] | Isopropyl Myristate | 8.00 |

TABLE 4-continued

| Ingredient | Chemical composition | % w/w |
|---|---|---|
| Light Mineral Oil | | 2.00 |
| Oil from example 1 | | 10.00 |
| Nipasol M [2] | Propylparaben | 0.10 |
| Water Phase | | |
| Carbopol 980 [3] (2% solution) | Carbomer | 7.50 |
| Nipagin M [2] | Methylparaben | 0.10 |
| Water | | 69.30 |
| pH adjuster | | |
| Triethanolamine | | qs |

[1] ex Croda
[2] ex Clariant
[3] ex Noveon

The cosmetic emulsion was prepared by adding the Carbopol 980 (2% solution) along with the Nipagin M to the water at room temperature with stirring and then heating to 75° C. The oil phase components were heated separately to 75° C. The oil phase components were then added to the water phase components with stirring and homogenised for 1 minute. The emulsion was then cooled down to 40° C. while stirring and the pH adjusted to ~6.0 with Triethanolamine.

EXAMPLE 4

A dermatological formulation in the form of a bath oil was prepared from the following ingredients in Table Five.

TABLE 5

| Ingredient | Chemical Composition | % w/w |
|---|---|---|
| Crodamol GTC C | Caprylic/capric triglycerides | 55.8 |
| Crodamol AB | C12-C15 alkyl benzoate | 8 |
| Crodamol EO | Ethyl oleate | 2 |
| Crodamol IPM | Isopropyl myristate | 2 |
| Crodamol IPP | Isopropyl palmitate | 2 |
| Tocopherol Acetate | Vitamin E | 0.2 |
| Volpo L3 Special | C12-C13 pareth-3 | 10 |
| Arlamol E | Polyoxypropylene-15 stearyl ether | 10 |
| Oil according to Example 1 | | 10 |

All ingredients are ex Croda except Tocopherol Acetate which is ex Roche

The bath oil was prepared by blending all the ingredients together at ambient temperature.

All of the features disclosed, and/or all of the steps of any method or process described, may be combined in any combination. Each feature disclosed herein may be replaced by alternative features serving the same, equivalent or similar purpose. Therefore, each feature disclosed is one example only of a generic series of equivalent or similar features.

The above statements apply unless expressly stated otherwise. The term specification, for these purposes, includes the description and any accompanying claims, abstract and drawings.

The invention claimed is:

1. A method of treating skin, mucosa, hair, nails, or scalp, comprising:
   administering to a subject in need thereof a human beta-defensin inducing agent comprising at least one triglyceride comprising a residue of:
   cis 7, 10, 13-hexadecatrienoic acid; linoleic acid; α-linoleic acid; γ-linoleic acid; stearidonic acid; eicosadienoic acid; dihomo-γ-linoleic acid; eicosatrienoic acid; eicosatetraenoic acid; arachidonic acid; eicosapentaenoic acid; docosadienoic acid; adrenic acid; docosapentaenoic acid; docosahexaenoic acid; or tetracosapentaenoic acid;

wherein the treatment exerts an antimicrobial effect on the skin, mucosa, hair, nails, or scalp of the treated subject.

2. The method of claim 1, wherein the human beta-defensin inducing agent is administered as a formulation.

3. The method of claim 2, wherein the formulation is a pharmacological formulation, a cosmetic formulation, or a dermatological formulation.

4. The method of claim 2, wherein the formulation comprises 0.01-20 wt. % of the human beta-defensin inducing agent.

5. The method of claim 1, wherein the at least one triglyceride comprises a residue of linoleic acid; α-linoleic acid; γ-linoleic acid; or stearidonic acid.

6. The method of claim 1, wherein the at least one triglyceride comprises:
   5 to 25% by weight linoleic acid;
   20 to 55% by weight α-linoleic acid;
   2 to 15% by weight γ-linoleic acid; and
   8 to 25% by weight stearidonic acid.

7. The method of claim 1, wherein the at least one triglyceride is a human beta-defensin inducing agent.

8. The method of claim 7, wherein the at least one triglyceride is a human beta-defensin 2 inducing agent.

9. The method of claim 1, wherein the at least one triglyceride is the main active ingredient in the manufacture of a cosmetic formulation used to exert the antimicrobial effect.

10. The method of claim 1, wherein the human beta-defensin inducing agent is administered orally or topically.

* * * * *